United States Patent [19]
Harding

[11] Patent Number: 5,613,978
[45] Date of Patent: Mar. 25, 1997

[54] ADJUSTABLE TIP FOR LANCET DEVICE

[75] Inventor: John D. Harding, Ben Lomond, Calif.

[73] Assignee: Palco Laboratories, Santa Cruz, Calif.

[21] Appl. No.: 659,056

[22] Filed: Jun. 4, 1996

[51] Int. Cl.$^6$ ................................................. A61B 17/32
[52] U.S. Cl. ............................................ 606/181; 128/770
[58] Field of Search ................................. 606/181–185; 128/770, 771

[56] References Cited

U.S. PATENT DOCUMENTS

| | | | |
|---|---|---|---|
| 4,469,110 | 9/1984 | Slama . | |
| 4,895,147 | 1/1990 | Bodicky et al. . | |
| 5,304,193 | 4/1994 | Zhadanov | 606/182 |
| 5,318,584 | 6/1994 | Lange et al. | 606/182 |
| 5,324,303 | 6/1994 | Strong et al. . | |
| 5,423,847 | 6/1995 | Strong et al. | 606/182 |
| 5,464,418 | 11/1995 | Schraga | 606/182 |
| 5,554,166 | 9/1996 | Lange et al. | 606/182 |

OTHER PUBLICATIONS

Boehringer Mannheim instruction sheet dated Jan. 93 for "Softclix" (German).

*Primary Examiner*—Michael Buiz
*Assistant Examiner*—William W. Lewis
*Attorney, Agent, or Firm*—Bruce H. Johnsonbaugh

[57] ABSTRACT

An adjustable tip for a blood lancet device for causing different depths of skin puncture is provided. An inner sleeve has a partially enclosed distal end which forms a stop for the shoulder of the lancet. An outer sleeve is pressed together with a cylindrical ring to form an internal camming surface, which captures a cam follower carried by the inner sleeve when the outer sleeve and cylindrical ring are slid as a unit on the inner sleeve. Rotation of the outer sleeve causes longitudinal motion between the distal ends of the inner and outer sleeve creating an adjustable double bottom which creates various puncture depths.

14 Claims, 5 Drawing Sheets

ADJUSTABLE TIP FOR LANCET DEVICE

BACKGROUND AND SUMMARY OF THE INVENTION

The present invention relates in general to a blood lancet device for obtaining a drop of blood for testing. In particular, the present invention provides an adjustable tip for a blood lancet device which allows for several different depths of skin puncture.

It is now general practice in developed countries for diabetics to test their blood sugar levels several times a day. This necessitates the use of some kind of finger lancing device to obtain a drop of blood for testing. Presently, most lancet devices have one or, at most, two different depths of skin puncture and depth is changed by removing the tip and replacing it with another. This is inconvenient since the extra tip must be carried about and can be misplaced. An improved system would allow for finer gradations of strike depth and allow adjustments to be made quickly without having to change tips. Most persons have slightly different thickness of skin on different fingers. For example, the index finger is commonly more calloused than the middle or ring fingers. By varying the puncture depth to just the right degree, pain can be minimized and, at the same time, an adequate drop of blood can be drawn for testing.

A prior art adjustable tip device, the "Softclix," is presently manufactured by the Boehringer Mannhelm Company. The "Softclix" tip can be termed a "single bottom" device because that area of the tip which rests against the skin is but a single layer of plastic.

In the Boehringer device, the end of the tip is threaded and skin puncture depth is adjusted by merely rotating the tip clockwise or counterclockwise. This straightforward method of depth adjustment is possible because Boehringer uses a custom lancet which is notched to fit precisely in the lancet carrier. Therefore, the lancet travels exactly the same distance each time that the Boehringer device is fired.

The most commonly used lancet does not avail itself of this simple solution to varying the depth of skin puncture. The generic lancet has no notch that would allow it to be positioned in exactly the same way each time it is loaded into the lancet carrier. A different method must therefore be used to reliably vary the depth of strike.

The prior art also includes the adjustable tip lancet mechanism of the Bodicky et al U.S. Pat. No. 4,895,147 dated Jan. 23, 1990. That patent teaches a relatively complex "single bottom" tip that includes a mechanism for applying a vacuum to the puncture site. The prior art also includes the Slama U.S. Pat. No. 4,469,110 dated Sep. 4, 1984. The Slama device adjusts penetration depth by rotating the threaded sleeve 10 relative to the body 2. The Slama device is a "single bottom" device using relatively expensive threads to achieve adjustable depth penetration. The patent does not teach a "double bottom" and does not teach means for holding the parts in position to achieve a given depth repeatedly.

The technique herein described uses a "double bottom" tip in which the shoulder of the lancet provides the stop to the lancet's movement when it abuts against the "inner bottom." The position of the "outer bottom" can be varied by the user by turning it against a helical camming surface. Molding of the helical groove is facilitated by placing the upper and lower surfaces of the groove in separate plastic parts which are then pressed together.

The present design allows all these objectives to be obtained while keeping the cost to a minimum since only three parts are needed to make the tip. The design also allows the tip to be made sufficiently small in diameter so that it matches the barrel size of commonly used pen-like devices. The entire device taken together is therefore aesthetically pleasing.

A primary object of the invention is to provide an adjustable tip for a blood lancet device capable of use with the most commonly used lancet presently available.

A further object of the invention is to provide an adjustable tip for a blood lancet device which is simple in design and relatively inexpensive to manufacture by using only three parts.

Further objects and advantages of the invention will become apparent from the following description and drawings wherein:

DETAILED DESCRIPTION OF THE DRAWINGS

Figures 1, 2, 3:
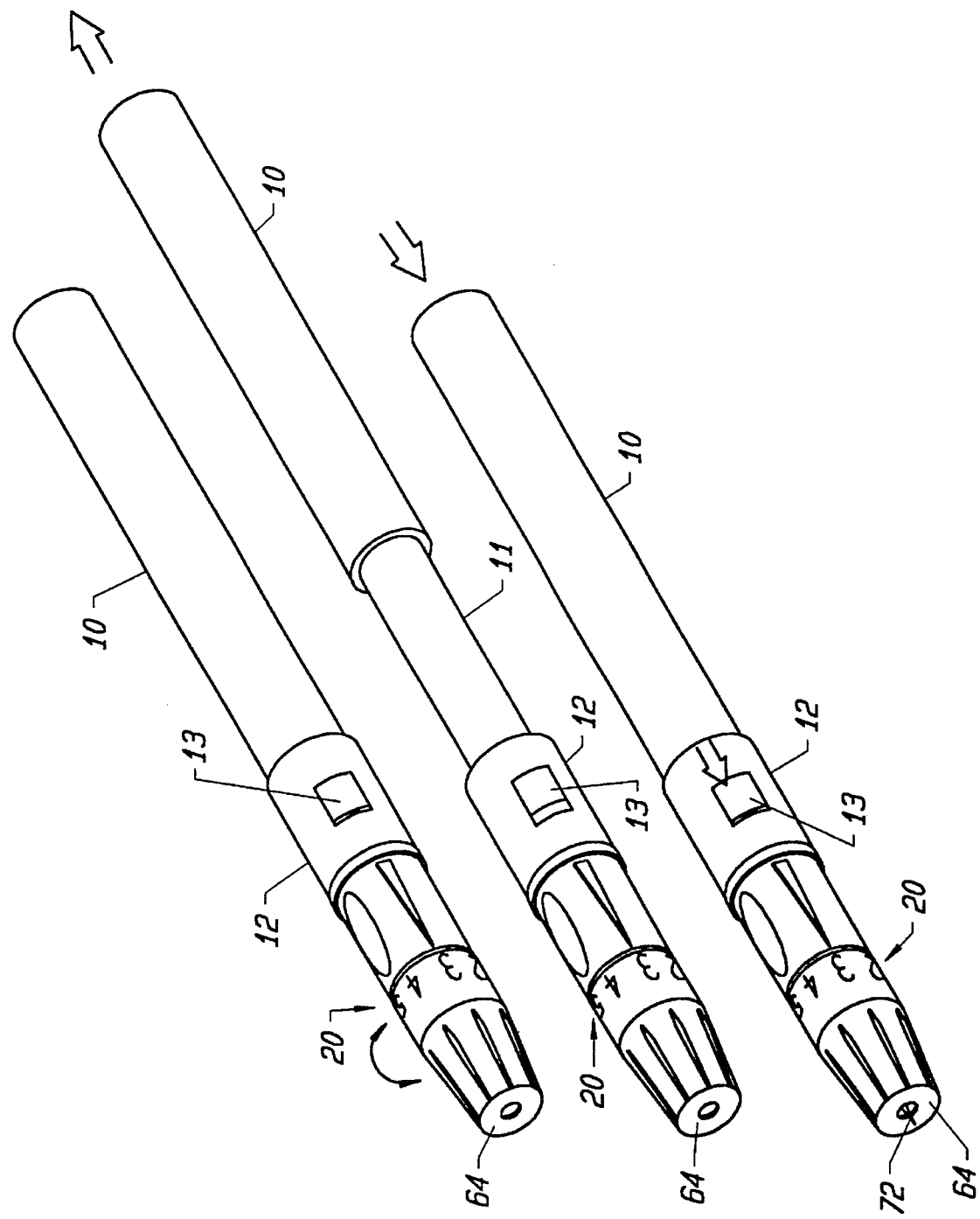
FIG. 1 is a perspective view of the adjustable tip of the present invention mounted on a base which is currently commercially available.
FIG. 2 is a perspective view of the device shown in FIG. 1 wherein the base portion is retracted to the position shown in FIG. 2 to compress an internal spring to prepare the device for making a strike.
FIG. 3 shows the device of FIGS. 1 and 2 as a strike is being made.

FIGS. 1, 2 and 3 show the adjustable tip lancet of the present invention as 20 mounted on a base member which includes collar 12 attached to a fixed tubular member 11. A slidable outer tube 10 is movable in the direction of the arrows shown in FIGS. 2 and 3 to compress an internal spring to prepare the lancet for a strike. The present invention relates to the adjustable tip 20 of FIGS. 1–3. The base of the instrument is essentially the same as shown in Levin et al U.S. Pat. Re. No. 32,922 dated May 16, 1989, incorporated herein by reference. The inside workings contained within fixed tube 11 and collar 12 are shown in detail in Pat. Re. No. 32,922 and are not repeated here.

Referring to FIG. 3 of the drawings, as the user depresses the trigger 13, the point 72 of the lancet needle is driven past the distal end 64 of the adjustable tip 20. The depth of the strike is readily adjustable as described in further detail below. In operation, the user presses the distal surface 64 against the surface of a finger, for example, and depresses trigger 13 which releases a compressed spring carried internally which in turn causes the needle point 72 to puncture the skin.

Figure 4:
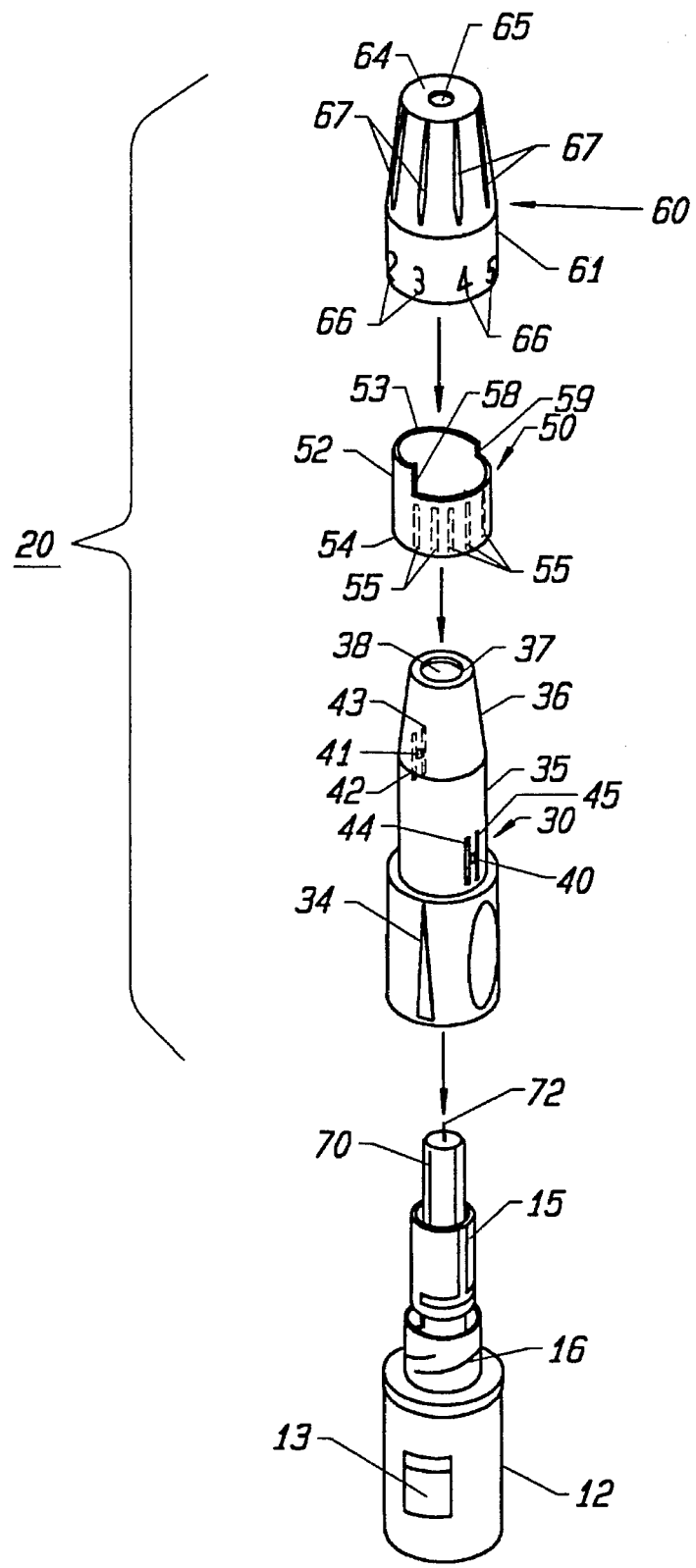
FIG. 4 is a perspective and exploded view of the adjustable tip of the present invention relative to a commercially available base on which the tip is mounted.

FIG. 4 shows an exploded view of the adjustable tip 20 which consists of three parts. Those parts include an inner sleeve, shown generally as 30, an intermediate cylindrical ring, shown generally as 50, and an outer cylindrical sleeve, shown generally as 60. The inner sleeve is carried by the base of the device shown partially in FIG. 4. The external threads 16 carried by the instrument base receive internal threads 39 of inner sleeve 30, as shown best in FIGS. 7 and 8. An internal plunger 15 carried by the base member is driven by an internal compressed spring (not shown) carried in the base and advances in the vertical direction shown in FIG. 4 when the trigger 13 is pressed by the user.

Figure 10:
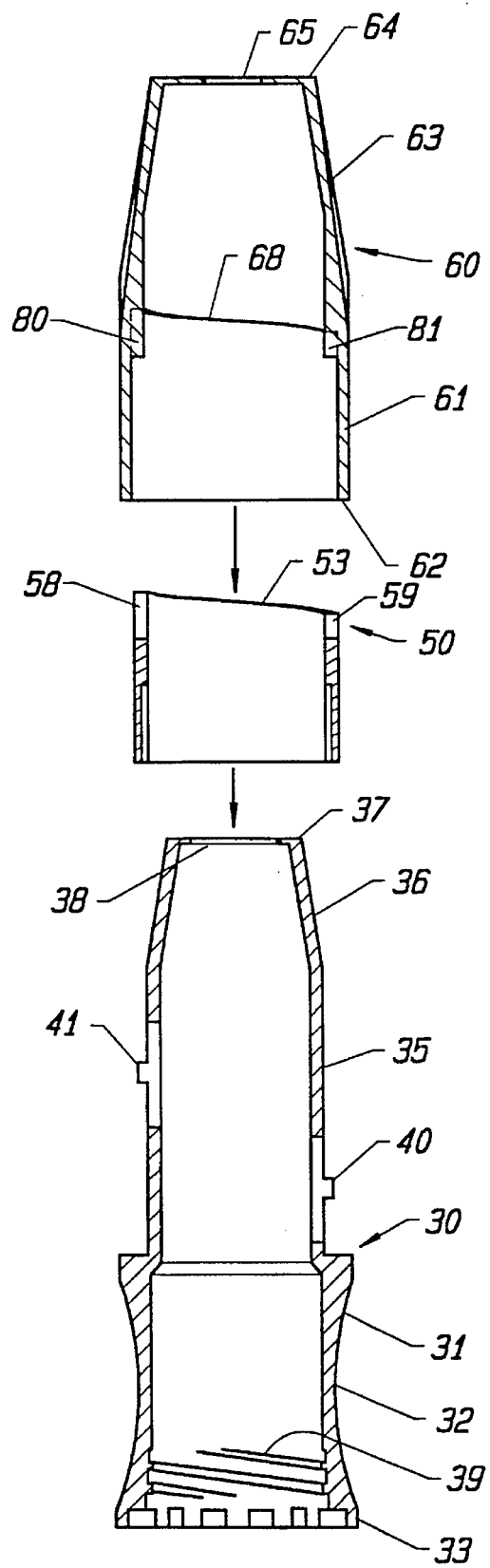
FIG. 10 is a sectional and exploded view of the adjustable tip of the present invention.

Inner sleeve 30 has a generally cylindrical shape center portion 35 having a proximal end 33 (FIG. 10) and distal end 37. Distal end 37 is partially enclosed to form a first surface against which the shoulder 74 of lancet 70 (FIG. 6) stops.

Figure 6:
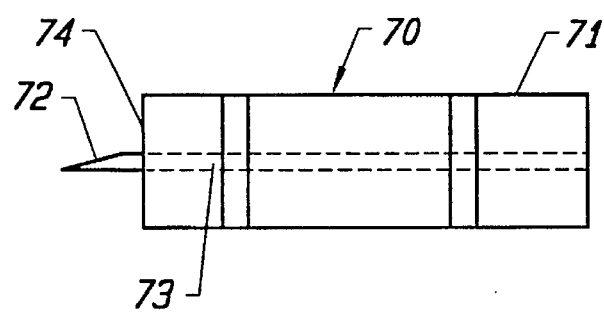
FIG. 6 is an elevational view of the most common and readily available lancet.

Referring to FIG. 6, the design of the most common and generic lancet 70 is shown. The lancet includes an elongated body 71, typically of plastic material, and an elongated needle 73 carried within the body 71. Needle 73 has a longitudinal axis extending along its length. A generally planar shoulder 74 perpendicular to said longitudinal axis forms one end of body 71 of the lancet. Needle 73 extends through shoulder 74 and a tapered point 72 is formed on the end of needle 73. As shown best in FIGS. 7 and 8, lancet 70 is carried inside inner sleeve 30 and is driven to the left in FIGS. 7 and 8 along said longitudinal axis when trigger 13 is depressed.

As shown best in FIG. 4, an intermediate cylindrical ring 50 has a proximal end 54 and a distal end 53. Distal end 53 extends approximately 180°, as shown best in FIG. 4, and preferably forms a helical incline camming surface, shown best in FIG. 10. The camming surface 53 may also be non-helical, but a helical design is preferred. Intermediate cylindrical ring 50 also has two vertical surfaces 58 and 59 extending downwardly from its distal end 53. The purpose of vertical surfaces 58 and 59 is to mate with vertical surfaces 80 and 81 of outer cylindrical sleeve 60 so that ring 50 and outer sleeve 60 rotate together in the assembled tip, as described below.

Intermediate cylindrical ring 50 also has a plurality of vertically extending grooves formed in the interior surface of ring 50. The grooves 55 engage lug or detent 40 carried by inner sleeve 30, as shown best in FIG. 5. As the intermediate cylindrical ring 50 is rotated relative to detent 40, detent 40 seats in one of the grooves 55 corresponding to one of the five depth indicators 66 of outer sleeve 60 (FIG. 4).

Figure 5:
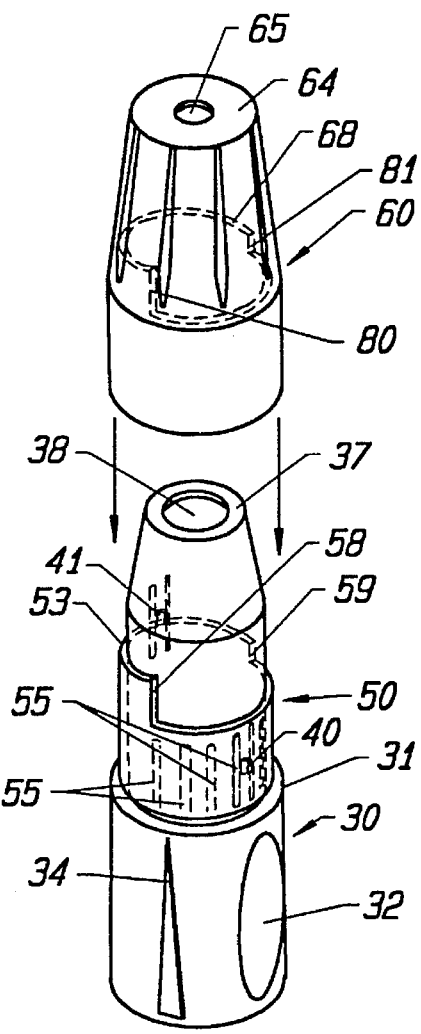
FIG. 5 is a perspective and partially exploded view of the adjustable tip according to the present invention.

Intermediate cylindrical ring 50 is adapted to slide onto inner sleeve 30 to the position shown in FIG. 5 and to rotate relative to inner sleeve 30.

Outer cylindrical sleeve 60 is adapted to slide over and to be press fitted onto the intermediate ring 50, as shown schematically in FIG. 5. The preferred method of assembly is to press together sleeve 60 and ring 50, and then slide the two joined together over sleeve 30. Thereafter 50 and 60, mated together, rotate as a unit relative to inner sleeve 30. When joined together, the upper and lower surfaces of the helix now form a complete helical groove which can capture a cam. Camming surfaces formed therein extend through an arc of approximately 180°. The outer sleeve 67 (FIG. 10) has a proximal end 62 and distal end 64. The distal end 64 is partially enclosed and has a circular opening 65 formed therein through which the point of the needle passes when a strike is made. First and second camming surfaces may be non-helical, but a helical design is preferred.

Assembly of the outer cylindrical sleeve 60 onto intermediate cylindrical ring 50 is accomplished by a press fit wherein sufficient pressure is required to connect the two pieces so that the user cannot disassemble those two pieces. It is significant that the outer sleeve 60 can be permanently attached to the intermediate ring 50 without requiring the use of sonic welding or the use of adhesives. The overall manufacturing cost of the present invention is therefore kept to a minimum while the simplicity of the design maximizes the useful life of the adjustable tip. Once the outer cylindrical sleeve 60 is pressed onto the intermediate cylindrical ring 50, the vertical surfaces 58 and 59 of the intermediate ring engage the vertical surfaces 80 and 81 carried on the outer cylindrical sleeve 60 and the two pieces rotate together. The indicating arrow or reference marker 34 carried at the base of inner sleeve 30 is used as a reference point to indicate which strike depth is set. As shown in FIG. 4, five strike depths are provided. Reference numerals 66 are applied to the outer surface of sleeve 60 in positions corresponding to grooves 55 in ring 50.

Figure 7:
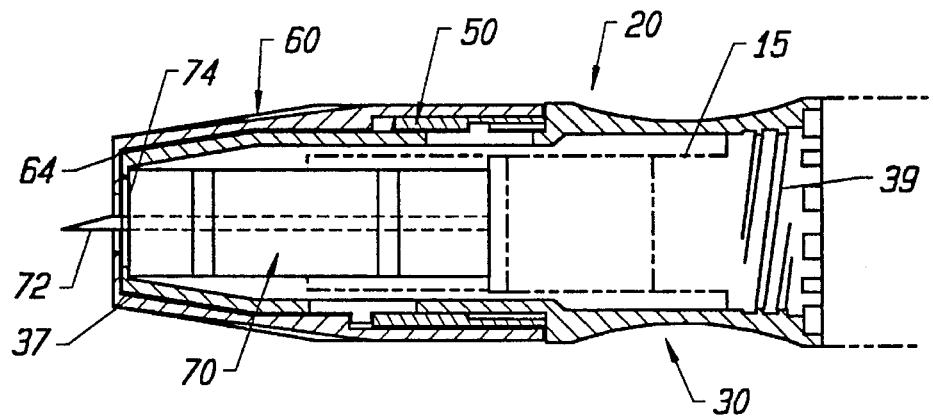
FIG. 7 is a sectional view of the adjustable tip as adjusted for maximum penetration.
Figure 8:
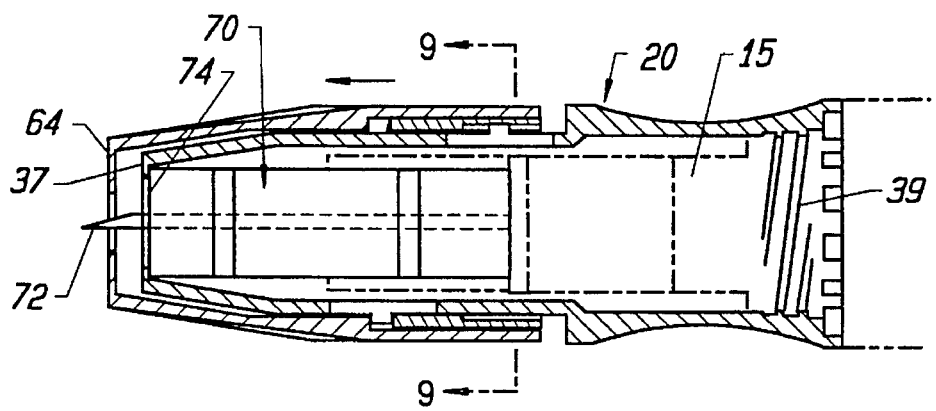
FIG. 8 is a sectional view of the adjustable tip of the present invention as adjusted for minimum penetration.

As shown best in FIGS. 7 and 8, the strike depth of the needle point 72 is adjusted by varying the longitudinal or axial distance between the distal end 64 of the outer sleeve 60 relative to the distal end 37 of the inner sleeve 30. Distal ends 64 and 37 form the "double bottom" aspect of the invention referred to above. FIG. 7 shows the maximum strike depth of the needle point 72 which is achieved when the distal end 37 of inner sleeve and distal end 64 of outer sleeve are adjacent each other. The position shown in FIG. 7 is achieved by rotation of the outer sleeve 60 in the clockwise direction as shown in FIGS. 4 and 5. Rotation in the clockwise direction causes the first camming surface 53 to pass under lug 41 carried by inner sleeve 30. Rotation of the outer sleeve 60 in the counterclockwise direction causes camming surface 68 to engage the upper surface of lug 41, in turn causing outer sleeve 60 to move in the direction of the arrow shown in FIG. 8 along the longitudinal axis of needle 73 to a position of minimum strike depth. The longitudinal axis of needle 73 is coincident with the longitudinal axis of the entire instrument as shown in FIGS. 1–3.

Outer sleeve 60 has a tapered upper portion 63 which has a plurality of grooves formed therein to facilitate rotation of sleeve 60 by the user. Inner sleeve 30 has a pair of opposed indents or depressions 32 formed therein which allows the user to grasp the base of inner sleeve 30 between a thumb and index finger of one hand and to rotate the outer sleeve 60 with the other hand. Reference marker arrow 34 is positioned between the opposed indents 32 to maximize visibility of the depth indicator numerals 66 which include the numerals "1" through "5."

It is to be understood that extension of the needle point 72 beyond the distal surface 64 of outer sleeve 60 occurs only momentarily as a strike is being accomplished. After the strike is performed, the needle is retracted into inner sleeve 30 to a rest position where the point 72 is not exposed.

Figure 9:
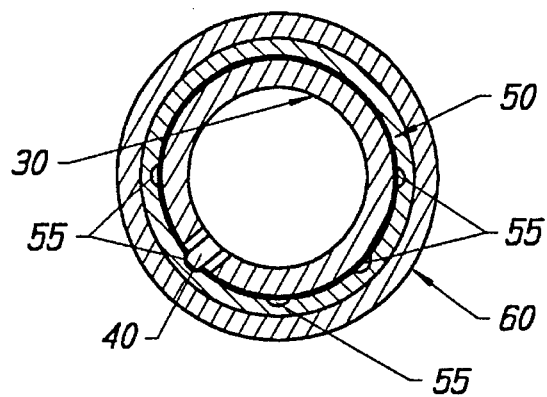
FIG. 9 is a section on the line 9—9 of FIG. 8.

FIG. 9 shows the location of five grooves 55 formed in the inner wall of intermediate cylindrical ring 50. Each of these grooves is located approximately 45° from each other. The maximum rotation of the outer sleeve relative to the inner sleeve is approximately 180°.

Each of the three parts comprising the adjustable tip, i.e. the inner sleeve 30, the intermediate ring 50 and the outer sleeve 60, may be injection molded, and assembled by an inexpensive press fit, thereby minimizing the overall manufacturing costs. The simplicity of the design maximizes the useful life of the device.

Cam follower 41 and detent 40 are resiliently carried on the outer surface of sleeve 30 by forming slits 42,43 and slits 44,45, respectively, in sleeve 30 adjacent thereto. Cam follower 41 has a rectangular cross-section for strength, as shown best in FIG. 10. The upper and lower surfaces of follower 41 are inclined to be parallel with camming surfaces 53 and 68 so that follower 41 moves smoothly against those surfaces.

The preferred method of assembly is to initially press together the intermediate ring 50 and outer sleeve 60. When pressed together (or attached by adhesive or even sonic welding as less preferable alternatives), ring 50 and sleeve 60 form a single part which has a smooth, interior groove formed by camming surfaces 53 and 68. The single part thus formed is then slid onto inner sleeve 30. Cam follower means 41 is resiliently carried by the outer surface of inner sleeve 30, allowing the single part thus formed to slide over it. Cam follower means 41 is "captured" by the groove formed by camming surfaces 53 and 68. Relative rotation of outer sleeve 60 with respect to inner sleeve 30 causes longitudinal motion of outer sleeve 60, as discussed above.

What is claimed is:

1. An adjustable tip for a blood lancet device for causing different depths of skin puncture, wherein said device utilizes a common lancet having an elongated body, a needle carried within said body wherein the point of said needle extends outwardly from said body, said body having a generally planar shoulder through which said needle extends, said adjustable tip comprising:

an inner sleeve through which said lancet passes, said sleeve having a generally cylindrical shape and having proximal and distal ends, said distal end being partially enclosed to form a first surface against which said shoulder of said lancet stops, and wherein said inner sleeve resiliently carries a cam follower, an intermediate cylindrical ring adapted to slide onto said inner sleeve and to rotate relative to said inner sleeve, said intermediate ring having a first camming surface formed therein, an outer, cylindrical sleeve, with open distal end, adapted to slide over said intermediate ring, said outer sleeve having a second camming surface, so that, when joined to the intermediate ring, a complete helical groove is formed which captures said cam follower.

2. An adjustable tip for a blood lancet device for causing different depths of skin puncture, wherein said device utilizes a common lancet having an elongated body, a needle carried within said body wherein the point of said needle extends outwardly from said body, said body having a generally planar shoulder through which said needle extends, said adjustable tip comprising:

an inner sleeve through which said lancet passes, said sleeve having a generally cylindrical shape and having proximal and distal ends, said distal end being partially enclosed to form a first surface against which said shoulder of said lancet stops, an intermediate cylindrical ring adapted to slide onto said inner sleeve and to rotate relative to said inner sleeve, said intermediate ring having a first camming surface formed therein, an outer, cylindrical sleeve adapted to slide over said intermediate ring, said outer sleeve having a second camming surface formed therein, said outer sleeve having proximal and distal ends, said distal end having an opening formed therein through which the point of said needle passes, means for connecting said outer sleeve to said intermediate ring, and a cam follower means carried by said inner sleeve so that, as said outer sleeve is rotated relative to said inner sleeve, the distal end of said outer sleeve moves relative to the distal end of said inner sleeve, said relative motion being caused by said first and second camming surfaces moving against said cam follower means.

3. The apparatus of claim 2 wherein said first and second camming surfaces are helical.

4. The apparatus of claim 2 wherein said intermediate cylindrical ring has a plurality of longitudinal grooves formed in its inner surface and said inner sleeve has a detent on its outer surface adapted to engage one of said longitudinal grooves.

5. The apparatus of claim 4 further comprising a plurality of indicating numerals applied to the outer surface of said outer sleeve, wherein at least one indicating numeral corresponds to each of said longitudinal grooves.

6. The apparatus of claim 5 wherein the proximal end of said inner sleeve has a pair of depressions formed on its outer surface, said depressions being located on opposite sides of said inner sleeve, said depressions allowing the user to grasp said inner sleeve between his thumb and index finger.

7. The apparatus of claim 6 further comprising a reference marker applied to the outer surface of said inner sleeve, between said depressions, allowing the user to easily see said indicating numerals and said reference marker while grasping said depressions with thumb and index finger.

8. The apparatus of claim 2 wherein each of said parts is plastic and is formed by injection molding.

9. An adjustable tip for a blood lancet device for causing different depths of skin puncture, wherein said device utilizes a common lancet having an elongated body, an elongated needle carried within said body and extending along a longitudinal axis, the point of said needle extending outwardly from said body, said body having a generally planar shoulder through which said needle extends, said adjustable tip consisting of only three parts prior to assembly:

an inner sleeve through which said lancet passes, said sleeve having a generally cylindrical shape and having proximal and distal ends, said distal end being partially enclosed to form a first surface against which said shoulder of said lancet stops, an intermediate cylindrical ring adapted to slide onto said inner sleeve and to rotate relative to said inner sleeve, said intermediate ring having a first camming surface formed therein, an outer, cylindrical sleeve adapted to be pressed onto said intermediate ring, said outer sleeve having a second camming surface formed therein, said outer sleeve having proximal and distal ends, said distal end having an opening formed therein through which the point of said needle passes, and a cam follower lug integrally formed on said inner sleeve so that, as said outer sleeve is rotated relative to said inner sleeve, the distal end of said outer sleeve moves axially along said longitudinal axis relative to the distal end of said inner sleeve, said relative axial motion being caused by said first and second camming surfaces moving against said cam follower.

10. The apparatus of claim 9 wherein said first and second camming surfaces are helical.

11. The apparatus of claim 10 wherein each of said three unassembled parts is plastic and is formed by injection molding.

12. An adjustable tip for a blood lancet device for causing different depths of skin puncture, wherein said device utilizes a common lancet having an elongated body, an elongated needle carried within said body and extending along a longitudinal axis, the point of said needle extending outwardly from said body, said body having a generally planar shoulder through which said needle extends, said adjustable tip comprising:

- an inner sleeve through which said lancet passes, said sleeve having a generally cylindrical shape and having proximal and distal ends, said distal end being partially enclosed to form a first surface against which said shoulder of said lancet stops,
- an intermediate cylindrical ring having a first camming surface formed therein,
- an outer, cylindrical sleeve means adapted to be pressed onto said intermediate ring, said outer sleeve means having a second camming surface formed therein whereby said first and second camming surfaces form a single, smooth groove, and said outer cylindrical sleeve means and said intermediate ring form a single part when pressed together, said outer sleeve having proximal and distal ends, said distal end having an opening formed therein through which the point of said needle passes, and
- a cam follower means resiliently mounted on the outer surface of said inner sleeve so that said single part formed by pressing together said outer sleeve means and said intermediate ring may be slid onto said inner sleeve, whereby said cam follower means is captured by said single, smooth groove, and relative rotation between said inner and outer sleeves will cause said distal end of said outer sleeve to move on said longitudinal axis relative to said distal end of said inner sleeve.

13. The apparatus of claim 12 wherein said first and second camming surfaces are helical.

14. The apparatus of claim 13 wherein said cam follower means has a generally rectangular cross-section and has upper and lower surfaces which are parallel with said first and second camming surfaces.

* * * * *

UNITED STATES PATENT AND TRADEMARK OFFICE
CERTIFICATE OF CORRECTION

PATENT NO. : 5,613,978
DATED : March 25, 1997
INVENTOR(S) : John D. Harding

It is certified that error appears in the above-indentified patent and that said Letters Patent is hereby corrected as shown below:

Col. 1, line 29, "Mannhelm" should read -- Mannheim --.

Signed and Sealed this

Twenty-fourth Day of June, 1997

Attest:

BRUCE LEHMAN

Attesting Officer

Commissioner of Patents and Trademarks